(12) United States Patent
Kroll

(10) Patent No.: US 7,373,202 B1
(45) Date of Patent: May 13, 2008

(54) UNIPOLAR AND BIPOLAR LEAD CARDIAC PACEMAKER AND METHOD FOR INHIBITING ANODE STIMULATION

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 307 days.

(21) Appl. No.: 11/096,979

(22) Filed: Mar. 31, 2005

(51) Int. Cl.
*A61N 1/00* (2006.01)

(52) U.S. Cl. .......................................................... 607/9

(58) Field of Classification Search .................... 607/9, 607/11, 119, 122, 66, 70, 72
See application file for complete search history.

(56) References Cited

U.S. PATENT DOCUMENTS

| | | | | |
|---|---|---|---|---|
| 4,170,999 | A | 10/1979 | Allen et al. | 128/419 PG |
| 4,406,286 | A | 9/1983 | Stein | 128/419 PG |
| 4,686,988 | A | 8/1987 | Sholder | 128/419 PT |
| 4,969,467 | A | 11/1990 | Callaghan et al. | 128/419 PG |
| 5,350,410 | A | 9/1994 | Kleks et al. | 607/28 |
| 5,411,540 | A | 5/1995 | Edell et al. | 607/53 |
| 5,431,689 | A | 7/1995 | Weinberg et al. | 607/14 |
| 5,782,880 | A | 7/1998 | Lahtinen et al. | 607/9 |
| 5,814,079 | A * | 9/1998 | Kieval | 607/4 |
| 5,935,160 | A | 8/1999 | Auricchio et al. | 607/122 |
| 5,978,709 | A | 11/1999 | Begemann et al. | 607/14 |
| 6,101,414 | A | 8/2000 | Kroll | 607/14 |
| 6,101,416 | A | 8/2000 | Sloman | 607/28 |
| 6,243,606 | B1 | 6/2001 | Mann et al. | 607/14 |
| 6,259,950 | B1 | 7/2001 | Mann et al. | 607/28 |
| 6,263,244 | B1 | 7/2001 | Mann et al. | 607/28 |
| 6,285,908 | B1 | 9/2001 | Mann et al. | 607/28 |
| 6,311,089 | B1 | 10/2001 | Mann et al. | 607/30 |
| 6,324,425 | B1 | 11/2001 | Blow et al. | 607/13 |
| 6,345,201 | B1 | 2/2002 | Sloman et al. | 607/28 |

(Continued)

FOREIGN PATENT DOCUMENTS

EP     1249254 A2     4/2002

(Continued)

OTHER PUBLICATIONS

Ranjan, Ravi et al., "*Mechanism of Anode Break Stimulation in the Heart*", Biophysical Journal, vol. 74 (Apr. 1998), pp. 1850-1863.

(Continued)

*Primary Examiner*—Carl Layno
*Assistant Examiner*—Jon-Eric C. Morales

(57) ABSTRACT

A multi-chamber implantable heart stimulation device is provided, adapted to inhibit anodal stimulation at a bipolar right chamber lead induced by a unipolar left chamber lead. The device includes a control unit adapted to provide to the unipolar left chamber lead a pace pulse having a trailing edge without a sharp cutoff. The control unit may be adapted to supply the pace pulse to the unipolar left chamber lead without a fast recharge period. The control unit may be adapted to supply to the unipolar left chamber lead a pace pulse having a trailing edge with a gradual decay, a ramp, steps, or a non-linear function. The control unit may be adapted to supply a different waveform to the bipolar right chamber lead than the pace pulse for the unipolar left chamber lead. For example, a conventional pacing pulse may be supplied to the bipolar right chamber lead.

8 Claims, 4 Drawing Sheets

U.S. PATENT DOCUMENTS

| | | |
|---|---|---|
| 6,421,564 B1 | 7/2002 | Yerich et al. .................. 607/9 |
| 6,421,566 B1 | 7/2002 | Holsheimer .................. 607/46 |
| 6,434,428 B1 | 8/2002 | Sloman et al. ................ 607/28 |
| 6,456,881 B1 | 9/2002 | Bornzin et al. ............... 607/27 |
| 6,456,882 B1 | 9/2002 | Schloss ........................ 607/28 |
| 6,477,417 B1 | 11/2002 | Levine ........................... 607/9 |
| 6,519,493 B1 | 2/2003 | Florio et al. .................... 607/9 |
| 6,572,557 B2 | 6/2003 | Tchou et al. ................ 600/483 |
| 6,645,153 B2 | 11/2003 | Kroll et al. .................. 600/481 |
| 6,675,046 B2 | 1/2004 | Holsheimer .................. 607/46 |
| 2001/0049543 A1 | 12/2001 | Kroll ............................ 607/28 |
| 2002/0193834 A1 | 12/2002 | Levine ........................... 607/9 |
| 2003/0120313 A1 | 6/2003 | Begemann et al. ............ 607/9 |

FOREIGN PATENT DOCUMENTS

| | | |
|---|---|---|
| EP | 1249254 A3 | 4/2002 |
| WO | WO 01/36040 A1 | 5/2001 |
| WO | WO 03/059446 A1 | 7/2003 |

OTHER PUBLICATIONS

Ranjan, Ravi et al., "*A Novel Mechanism of Anode-Break Stimulation Predicted by Bidomain Modeling*", Circ Res. 1999;84:153-156.

* cited by examiner

UNIPOLAR AND BIPOLAR LEAD CARDIAC PACEMAKER AND METHOD FOR INHIBITING ANODE STIMULATION

BACKGROUND

Conventional Implantable Cardiac Devices (FIGS. 1 and 2)

FIG. 1 shows a conventional stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage, and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

FIG. 2 illustrates a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar capabilities would exist on the atrial channel with respect to tachycardias occurring in the atrium. These would be atrial tachycardias (AT), more rapid atrial tachycardias (Atrial Flutter) and atrial fibrillation (AF).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller may include a capture-based tachycardia detection unit, which operates to detect a tachycardia based on loss of capture of pacing pulses. In the primary example described herein, the tachycardia detection unit operates to detect AF based on loss of capture of atrial pacing signals during preventive overdrive pacing in the atrium. Accordingly, the capture-based tachycardia detection unit is used in conjunction with a preventive overdrive pacing unit for controlling overdrive pacing of the heart. One particularly effective overdrive pacing technique, referred to herein as dynamic atrial overdrive (DAO) pacing, is described in U.S. Pat. No. 6,519,493 to Florio et al., entitled METHODS AND APPARATUS FOR OVERDRIVE PACING HEART TISSUE USING AN IMPLANTABLE CARDIAC STIMULATION DEVICE, which is incorporated by reference herein. With DAO, the overdrive rate is controlled to remain generally uniform and, in the absence of a tachycardia, is adjusted upwardly or downwardly only occasionally. Dynamic overdrive techniques are also applicable to the ventricles. Exemplary dynamic ventricular overdrive (DVO) techniques are described in U.S. patent applications: 1) Ser. No. 10/456,060 to Park et al., entitled SYSTEM AND METHOD FOR DYNAMIC VENTRICULAR OVERDRIVE PACING, filed Jun. 6, 2003 Ser. No. 10/456,058, entitled SYSTEM AND METHOD FOR DYNAMIC VENTRICULAR OVERDRIVE PACING, Jun. 6, 2003, which applications are also incorporated herein by reference. In one example, the overdrive pacing unit operates continuously in the absence of a tachycardia so as to reduce the likelihood of the onset of a tachycardia. In other examples, preventive overdrive pacing is suspended while the patient is asleep. It is also suspended when the patient is in a tachycardia that has resulted in the enabling of the Automatic Mode Switch algorithm. In any case, if a tachycardia is detected during preventive overdrive pacing by the tachycardia detection unit, an ATP unit is activated to deliver antitachycardia pacing to the heart in an effort to terminate the tachycardia.

The ATP unit may administer ATP in accordance with any of a variety of ATP techniques. Exemplary patents describing ATP techniques include U.S. Pat. No. 6,101,414, to Mark Kroll, entitled METHOD AND APPARATUS FOR ANTITACHYCARDIA PACING WITH AN OPTIMAL COUPLING INTERVAL, and U.S. Pat. No. 5,431,689 to Weinberg et al., entitled IMPLANTABLE STIMULATION SYSTEM AND METHOD FOR TERMINATING CARDIAC ARRHYTHMIAS, which are both incorporated by reference herein. Tachycardia may be detected during preventive overdrive pacing based, for example, upon detection of a true loss of capture of a preventive overdrive pacing pulse or upon detection of a loss of capture of a backup pulse subsequent to a PAC.

To detect loss of capture, the microcontroller also includes an automatic capture detection unit for detecting an evoked response from the heart in response to an applied stimulus. The capture detection unit verifies capture of both primary pacing pulses and any subsequent backup pulses. Capture occurs when an electrical stimulus applied to the heart is of sufficient energy to depolarize the cardiac tissue, thereby causing the heart muscle to contract. The capture detection unit detects a depolarization signal during a window following a stimulation pulse, the presence of which indicates that capture has occurred. Capture detection is performed on a beat-by-beat basis. If a primary pulse is not captured, a backup pulse unit delivers a backup pulse at a maximum pulse magnitude. The capture detection unit also detects whether the backup pulse captures.

Also included is a stimulation threshold search unit for automatically determining the current capture threshold of the patient, i.e. the minimum output sufficient to evoke capture, so that the output or pulse magnitude can be reset properly. This is commonly reported in terms of pulse amplitude as this is one of the programmable output parameters. While preventive overdrive pacing is performed, a stimulation search is automatically performed in circumstances wherein a primary pacing pulse is not captured but the backup pulse is captured. (If both the overdrive pulse and the backup pulse are not captured, ATP is instead activated.) Also, preferably, a capture threshold search is performed periodically to update the capture threshold regardless of whether any loss of capture is detected. Such capture threshold searches are preferably performed every eight hours. Typically, a capture threshold search begins at a desired starting point (either a high energy level or the level at which capture is currently occurring) and decreases the energy level until capture is lost. It then increments the output in 0.125 Volt steps until capture is restored. The value at which capture is restored is known as the capture threshold. Thereafter, a working margin or a safety margin is added to the capture threshold to yield a new pulse magnitude. A safety margin is a fixed multiple of the measured threshold. A working margin is a fixed value, e.g. 0.25 Volts above the measured threshold. In one implementation, the safety margin is provided by the high output backup pulse. The delivered output associated with the primary pulse is simply a working margin above the measured capture threshold.

Various techniques for implementing capture verification of atrial pacing pulses (i.e. atrial AutoCapture) are set forth in U.S. Pat. Nos. 6,434,428 to Sloman et al.; 6,311,089 to Mann et al.; 6,285,908 to Mann et al.; 6,263,244 to Mann et al.; 6,259,950 to Mann et al.; 6,243,606 to Mann et al.; and 6,101,416 to Sloman, which are incorporated herein by reference. Capture verification of ventricular pulses is described in 6,456,882 to Schloss; 6,456,881 to Bornzin et al.; and 6,345,201 to Sloman, et al, which are also incorporated herein by reference. See also U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. A technique for implementing automatic capture verification during overdrive pacing is described in U.S. patent application Ser. No. 10/138,438, filed May 2, 2002, of Bradley et al., entitled METHOD AND APPARATUS FOR PROVIDING ATRIAL AUTOCAPTURE IN A DYNAMIC ATRIAL OVERDRIVE PACING SYSTEM FOR USE IN AN IMPLANTABLE CARDIAC STIMULATION DEVICE, which is incorporated herein by reference.

The microcontroller also includes a PAC detection unit 109 and a PAC response unit. The PAC detection unit detects PACs and the PAC response unit provides a pacing protocol for responding to the PAC. An exemplary PAC response protocol is described in U.S. Pat. No. 5,978,709 to Begemann et al., entitled PACEMAKER SYSTEM WITH IMPROVED TECHNIQUES FOR PREVENTING AND SUPPRESSING ATRIAL ARRHYTHMIAS, which is incorporated herein by reference.

Although shown as being components of the microcontroller, any or all of capture-based tachycardia detection unit, overdrive pacing unit, ATP unit, capture detection unit, stimulation threshold search unit, PAC detection unit, PAC response unit, and backup pulse unit could be instead implemented as separate components. Also, depending up on the particular component and the particular implementation, individual components may be configured to apply to the ventricles, the atria, or in some cases both.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. (V-V delay is typically used in only connection with independently programmable RV and LV leads for biventricular pacing.) While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate antitachycardia pacing therapy or electrical shock therapy to the heart aimed at terminating the detected arrhythmia. To this end, the microcontroller 60 further controls a shocking circuit by way of a control signal. The shocking circuit generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are of relatively low to moderate energy level (so as to minimize the current drain on the battery) and are usually between 5 to 20 joules. Typically, cardioversion shocks are synchronized with an R-wave. Defibrillation shocks are generally of moderate to high energy level (i.e., corresponding to thresholds in the range of 15 to 40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Congestive Heart Failure

Clinical evidence is revealing that patients suffering from cardiac diseases which affect the contractility of the heart muscle tissue rather than the conduction pathways, generally known as congestive heart failure or CHF, can benefit from cardiac pacing. CHF is a condition in which a weakened heart cannot pump enough blood to body organs. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Treatment typically involves pacing on both sides of the heart. In such patients, pacing in the atria and ventricles effectively resynchronizes heart chamber contractions thereby improving hemodynamic function of the heart. Biventricular pacing has proven to be an effective therapy or treating patient with congestive heart failure.

A system and method for monitoring progression of cardiac disease state using physiologic sensors is disclosed in U.S. Pat. No. 6,572,557, by Tchou, et al., issued Jun. 3, 2003, which describes a technique for monitoring physiological parameters associated with the progression, stabilization, or regression of symptoms of heart disease such as congestive heart failure (CHF), which is herein incorporated by reference in its entirety. A system and method for evaluating risk of mortality due to congestive heart failure using physiologic sensors is disclosed in U.S. Pat. No. 6,645,153 by Kroll et al., issued Nov. 11, 2003, which is herein incorporated by reference in its entirety. One method and apparatus for biventricular stimulation and capture monitoring is disclosed in published U.S. Patent application publication number 20010049543, filed May 1, 2001, by Mark Kroll, herein incorporated by reference in its entirety.

For CHF the left side of the heart, as well as the right is paced. Unfortunately, when fitting a patient with an implantable pacing device, it can be difficult to pass a left-side lead into the coronary sinus vein, or the smaller final destination veins. To facilitate left side lead 24 implantation, the left side lead 24 may be unipolar, with a tip 26, but without the ring 27 shown in FIG. 1. The case 10 could be used as the return, but it sometimes causes stimulation of the muscle surrounding the case, which is uncomfortable to the patient. As an alternative, the ring 34 of the right ventricle lead 30 is used as the return path. Not only does this allow high current density around the tip 26 in the left ventricle for pacing, it also causes high current density around the ring 34. If the ring 34 is in contact with the heart muscle, it will stimulate the right ventricle along with the left ventricle. This is sometimes referred to as anodal stimulation.

Anodal stimulation causes the right ventricle to pace at the same time as the left ventricle. Ideally, however, the right side should be stimulated 20-40 milliseconds after the left side. If both sides are stimulated at the same time rather than 20-40 milliseconds apart, the patient can feel faint as the heart is not pumping as much blood.

Accordingly, what is needed is device that allows biventricular pacing with a unipolar left ventricle lead without causing anodal stimulation in the right ventricle. Moreover, what is needed is a means to inhibit anodal stimulation in patients being treated with bi-chamber pacing for congestive heart failure.

SUMMARY

In certain embodiments, a multi-chamber implantable heart stimulation device is provided which is adapted to inhibit anodal stimulation at a bipolar right chamber lead induced by a unipolar left chamber lead. The implantable heart stimulation device may include a control unit adapted to provide to the unipolar left chamber lead with a pace pulse having a trailing edge without a sharp cutoff.

The control unit may be adapted to supply to the unipolar left chamber lead a pace pulse having a trailing edge with a gradual decay, a ramp, steps, or a non-linear function. In one embodiment, the control unit may be adapted to supply the pace pulse to the unipolar left chamber lead without a fast recharge period. The control unit may be adapted to supply a different waveform to the bipolar right chamber lead than the pace pulse for the unipolar left chamber lead. As such, a conventional pacing pulse may be supplied to the bipolar right chamber lead.

In certain embodiments, a multi-chamber implantable heart stimulation device is provided which includes a unipolar left chamber lead, a bipolar right chamber lead, and a control unit adapted to supply the unipolar left chamber lead with a pace pulse having a trailing edge slope which has a magnitude below a threshold sufficient to inhibit capture of a right chamber by anodal break stimulation of the right chamber.

In one implementation, a method is provided for biventricular pacing adapted for treating congestive heart failure which includes supplying a pace pulse to a unipolar lead adapted for left ventricle stimulation and then supplying a pace pulse to a bipolar lead adapted for right ventricle stimulation. The method further includes configuring the bipolar lead as the anode for the unipolar lead and constructing a pace pulse for the unipolar lead which includes a trailing edge having slope of sufficiently small magnitude to inhibit capture of the right ventricle by anode break stimulation.

DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
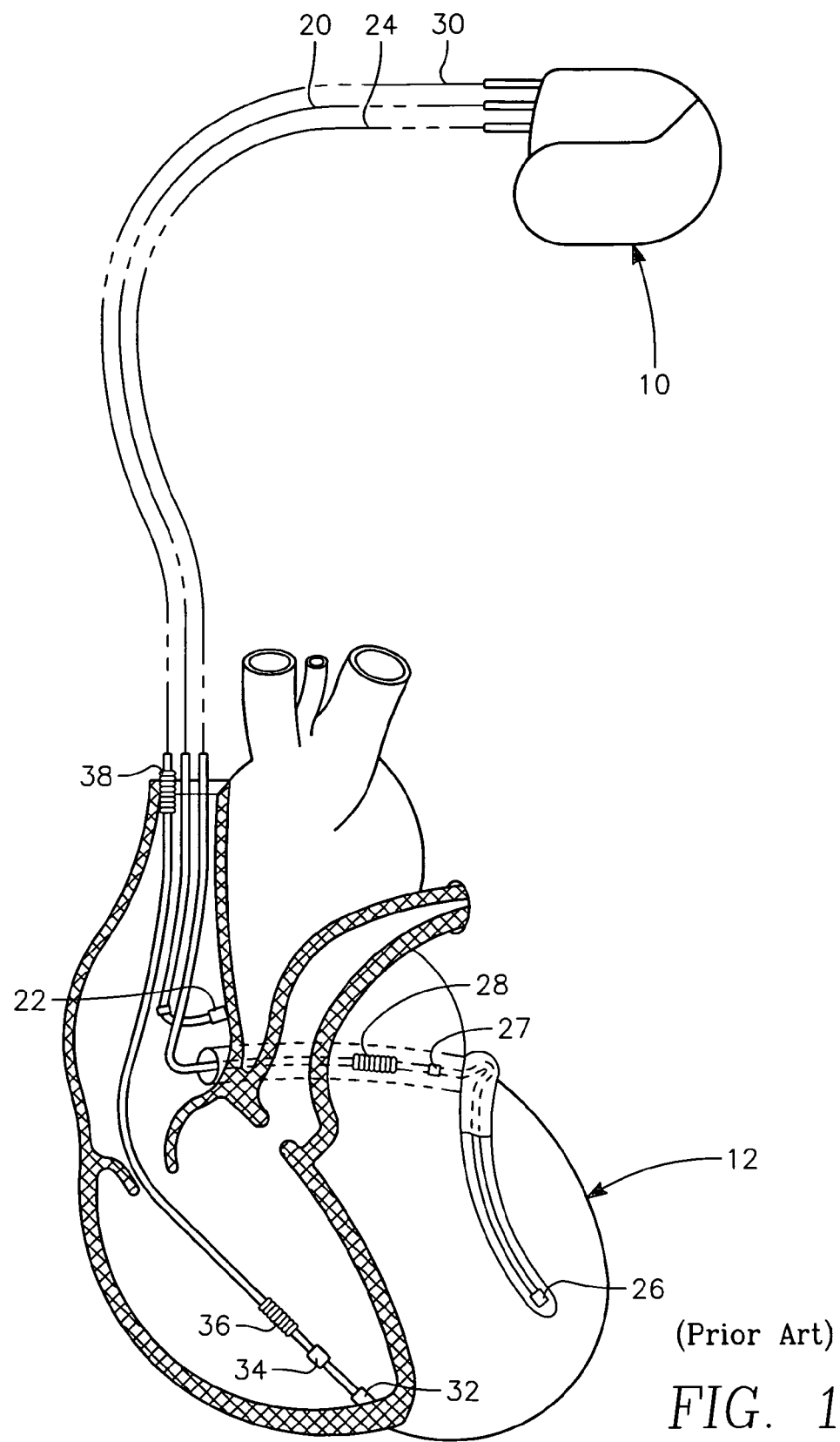
FIG. 1 shows a conventional stimulation device.
Figure 2:
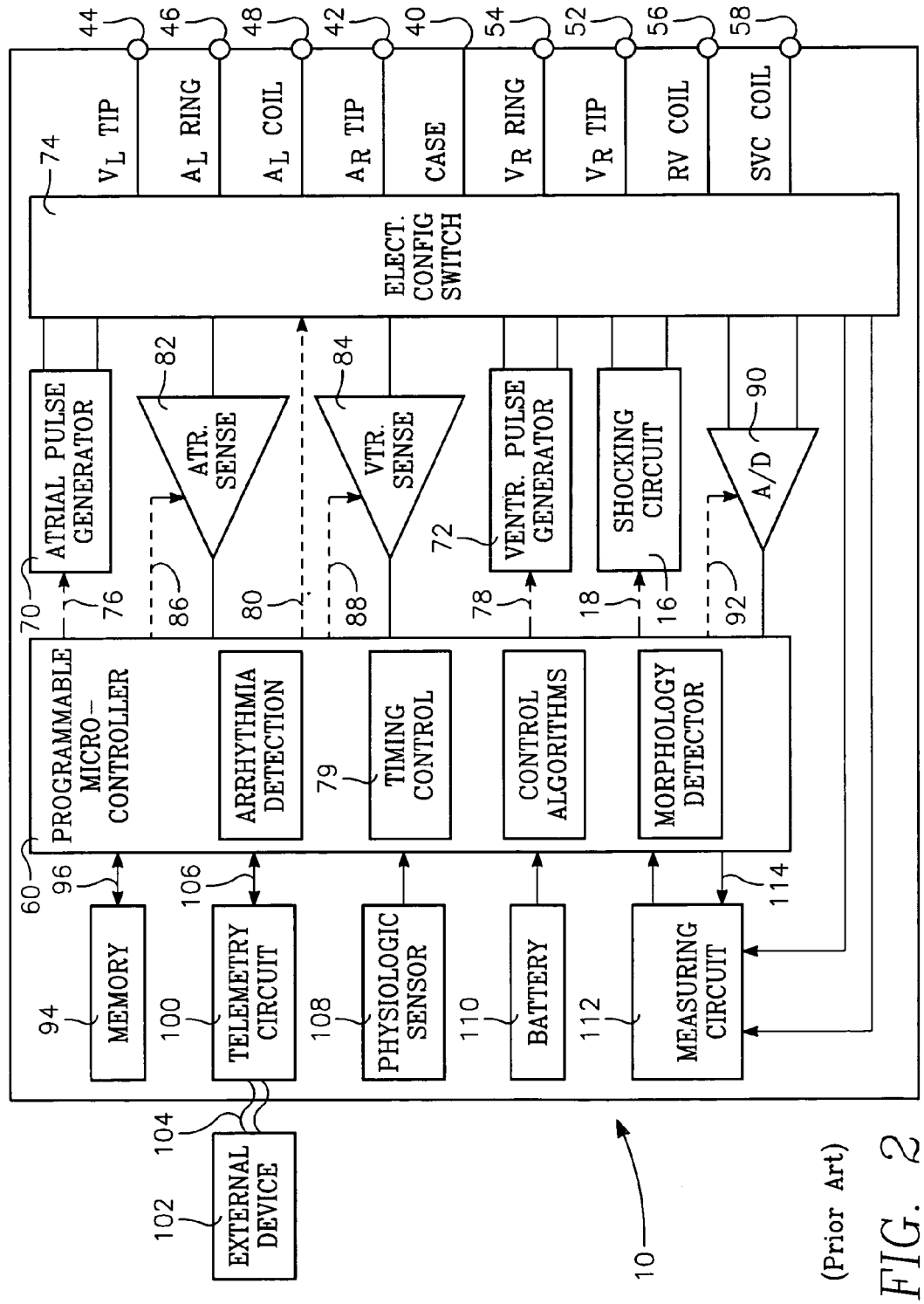
FIG. 2 illustrates a simplified block diagram is shown of the multi-chamber implantable stimulation device.
Figure 3A:
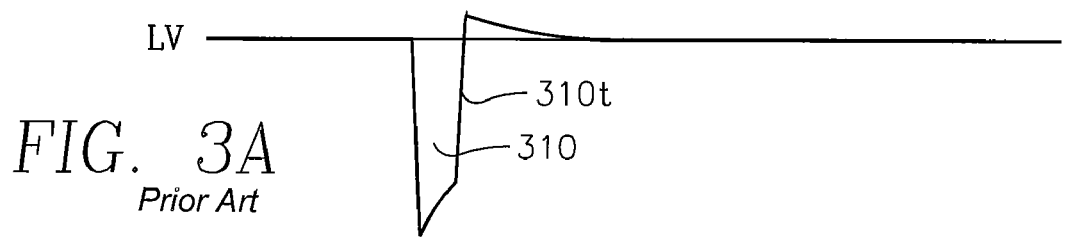
FIGS. 3A and 3B show pulse timing diagrams of left ventricle and right ventricle pacing pluses, respectively, for conventional biventricular pacing.
Figure 3B:
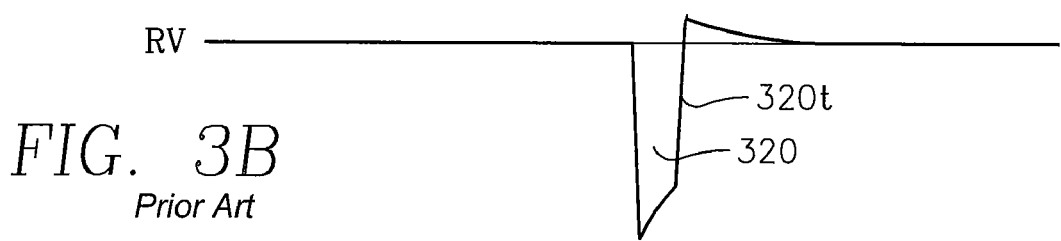

FIGS. 3A and 3B show pulse timing diagrams of conventional right ventricle and left ventricle pacing pluses 310 and 320, respectively. A conventional CHF pacing system includes two identical pulses 310 and 320 for the left and right ventricles, respectively. In most CHF therapy situations, the normal V-V delay is greater than 20 milliseconds to about 100 milliseconds, typically about 40 milliseconds, for example. The trailing edges 310t and 320t of the pacing pulses 310 and 320, respectively, each have a sharp break, and a steep, near infinite slope. Output amplifier circuits incorporate fast recharge circuitry to shorten the time to restore the voltage potential of the electrodes after stimulation. Fast recharge circuitry and operations are described in U.S. Pat. Nos. 4,406,286 by Stein; 4,170,999 by Allen et al.; 5,782,880 by Lahtinen et al.; and 6,324,425 by Blow et al., all incorporated herein by reference.

As such, state of the art pacemakers now include the fast recharge operation. This ensures that the coupling capacitor (s) is recharged to an insignificant voltage level or equilibrium prior to the delivery of the next pacing pulse through it. Also, it allows the net DC current in the pacing path to settle to zero to facilitate sensing in the same pacing path using one of the pace/sense electrodes of that pacing path.

Fast recharge in a unipolar electrode arrangement, however, can precipitate anodal break stimulation at the trailing edge of the pulse if the return path ring electrode in the right chamber is too close to the heart muscle. As discussed above, this can cause inefficient pumping by the heart.

As conventional understanding of the heart mechanisms does not adequately explain anode break stimulation in the heart, several theories have emerged to form models of anode break stimulation in the heart. See for example, "Mechanism of Anode Break Stimulation in the Heart," by Ranjan et al., printed in the Biophysical Journal, Vol. 74, pp. 1850-63, April 1998; and "A Novel Mechanism of Anode-Break Stimulation Predicted by Bidomain Modeling," by Ranjan et al., Circulation Research, Vol. 84, pp. 153-156, Feb. 5, 1999, available at http://www.circresaha.org, both herein incorporated by reference. Due to the complexities and unique nature of heart tissue, there is no practical means to inhibit anodal break stimulation in the heart. Thus, for bi-ventricular pacing using a unipolar left ventricular lead it is possible that simultaneous stimulation of the right and left ventricles will occur if the right ventricular ring electrode is positioned too close to the heart tissue.

Figure 4A:
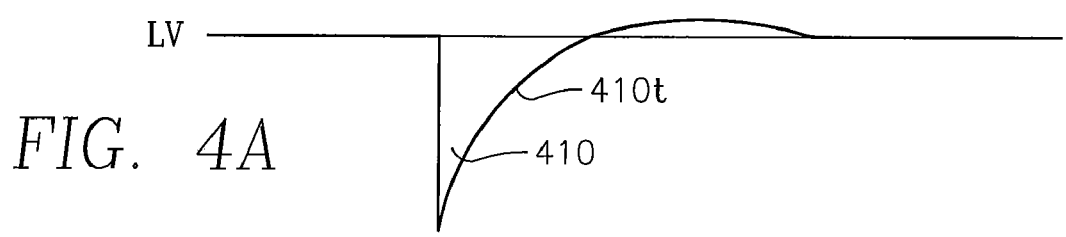
FIGS. 4A and 4B show pulse timing diagrams of left ventricle and right ventricle pacing pluses in accordance with one implementation of the present invention.
Figure 4B:
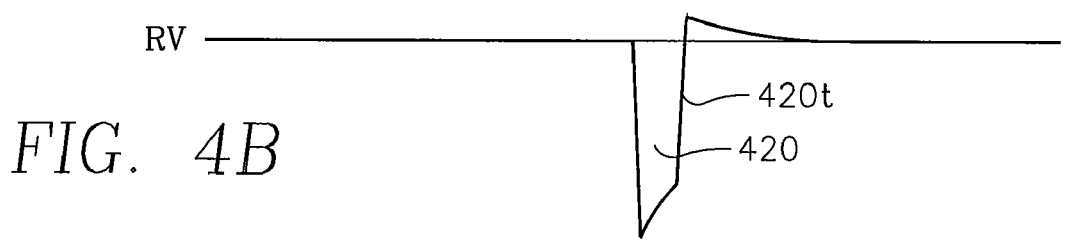

FIGS. 4A and 4B show pulse timing diagrams of left ventricle and right ventricle pacing pluses 410 and 420, respectively, in accordance with one implementation of the present invention. To inhibit anodal break stimulation in CHF patients fitted with bi-ventricular unipolar leads, the left ventricular pulse 410 is provided without a sharp break at the trailing edge 410t of the left ventricular pulse 410. Thus, the average slope of the trailing edge is reduced from that of the conventional pacing pulse 310 shown in FIG. 3A. In one implementation, this may be accomplished by eliminating the fast recharge period normally associated with the left ventricular pulse 310 shown in FIG. 3A. The fast recharge abruptly truncates the left ventricular pulse 310. Instead, the left ventricle electrode may be allowed to recharge without a fast recharge circuit. The output capacitor associated with the left ventricle electrode may be merely discharged through the heart, so there is no "break" of current to cause "anodal break" stimulation. Instead there is a gradual recharge of the output capacitor. The left ventricle pulse, then, has a trailing edge exhibiting a gradual exponential decay rather than a sharp cutoff at the trailing edge.

The right ventricular pulse 420, however, may include a conventional fast recharge period which has a trailing edge 420t with a near infinite slope. Thus, the left and right ventricle pulses 410 and 420 are not identical in some implementations. In other implementations, however, it is possible to provide a right ventricular pulse with the same characteristics as the left ventricular pulse.

In some implementations, the average slope of the trailing edge may be reduced using a gradual recharge circuit to provide a trailing edge having a ramp, rounded, curved, multi-stepped, plateaued, graduated, or the like, to inhibit anodal break stimulation of the right ventricle. Thus, in some implementations, the average slope of the trailing edge 410t may reduced by applying a slow or an intermediate recharge for a gradual recharge, rather than the sharp cutoff trailing edge 310t shown in FIG. 3A.

Figure 5A:
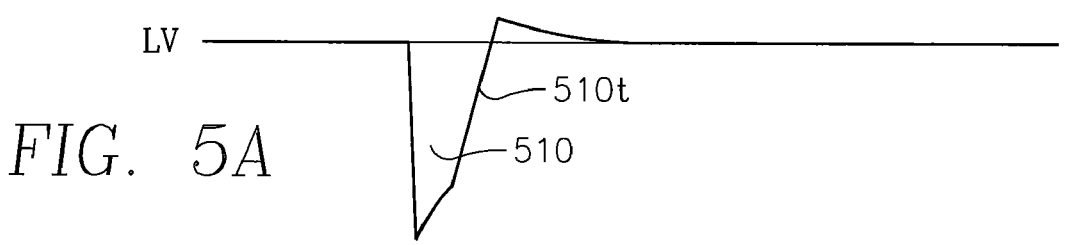
FIGS. 5A and 5B show pulse timing diagrams of left ventricle and right ventricle pacing pluses in accordance with one implementation of the present invention.
Figure 5B:
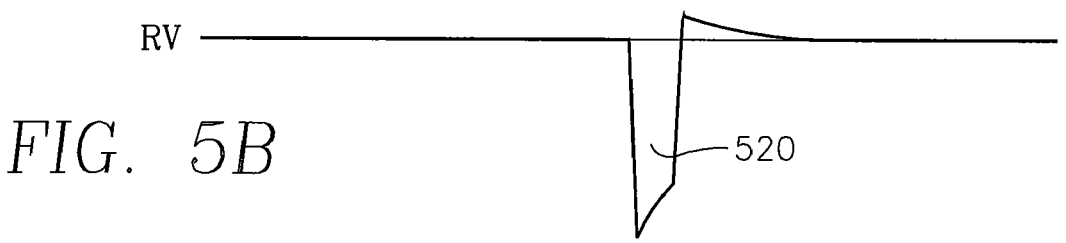

FIGS. 5A and 5B show pulse timing diagrams of left ventricle and right ventricle pacing pluses 510 and 520, respectively, in accordance with one implementation of the present invention. In this implementation, the left ventricular pulse 510 may have a ramped trailing edge 510t. Removing the steep, near infinite slope caused by conventional fast recharge inhibits capture of a right ventricle by anodal break stimulation and instead allows the right ventricle cathode to capture and pace the right ventricle with a pacing pulse applied after a V-V delay period. The trailing edge of the pacing pulse should have a slope that is below a threshold sufficient to inhibit capture of a right chamber by anodal break stimulation of the right chamber. It is expected a gradual recharge that extends beyond a conventional fast recharge period, which is typically about a microsecond, would inhibit anodal break stimulation. In most implementations, the recharge duration has a value in a range from about 10 microseconds to about 1 millisecond, or up to about 3 milliseconds to provide a more gradual recharge. In a typical implementation, the recharge duration is around 100 microseconds. The threshold for each type of gradual recharge can be determined through empirical means.

Figure 6:
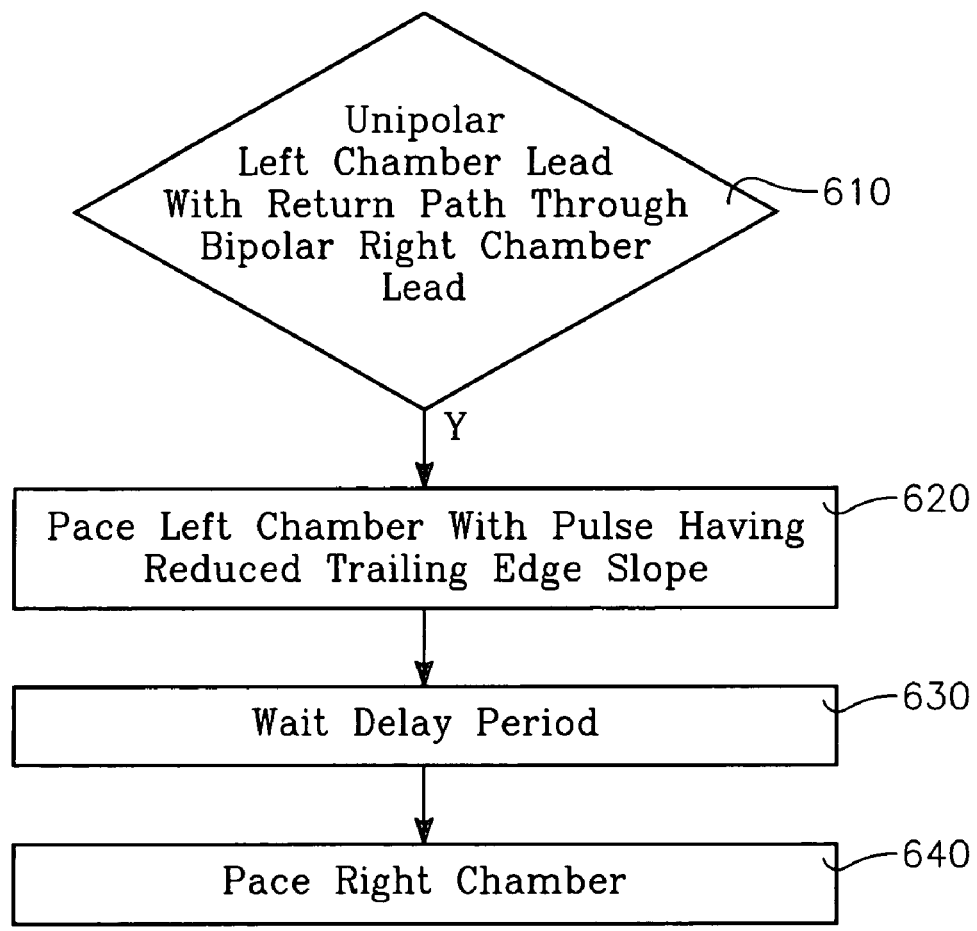
FIG. 6 is a flow diagram of a method in accordance with one possible implementation of the present invention.

FIG. 6 is a flow diagram of a method in accordance with one possible implementation of the present invention. If bi-chamber pacing therapy is to be administered through a unipolar left chamber lead with a return path through a bipolar right chamber lead 610, the left chamber is paced with a pulse having a reduced trailing edge slope 620. One way to accomplish this is to omit the fast recharge of the left chamber electrode, and instead allow a non-driven gradual recharge. In other implementations, a gradual recharge in the form of a ramp, multi-step, graduated, non-linear function, or the like is applied to provide a reduced trailing edge slope to inhibit anodal break stimulation.

Referring to FIG. 6, after waiting a delay period 630, i.e. V-V delay, the right chamber is paced 640. The right chamber may be paced with conventional pacing, which can incorporate a fast recharge following the left chamber pacing pulse. The method of FIG. 6 can be utilized in CHF therapy to inhibit anodal break stimulation from causing both chambers of the heart to beat at the same time.

As can be appreciated a wide variety of techniques can be implemented consistent with the principles of the invention and no attempt is made herein to describe all possible embodiments and implementations. Although described primarily with reference to congestive heart failure, the principles of the invention are applicable to other implanted cardiac stimulation devices as well, such as pacemakers without congestive heart failure therapy capability. Furthermore, although some figures above were discussed with reference to bi-ventricular stimulation for example purposes, it should be understood that implementations of the present invention may be utilized in bi-atrial stimulation. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for biventricular pacing, the method comprising:

a) supplying a pacing pulse to a unipolar lead adapted for stimulation of a left ventricle;

b) supplying a pace pulse to a second lead adapted for stimulation of a right ventricle;

c) configuring the second lead to provide an anode for the unipolar lead; and d) constructing the pace pulse to the unipolar lead to comprise a trailing edge having slope of sufficiently small magnitude to inhibit capture of the right ventricle by anode break stimulation at the anode.

2. The method of claim 1 wherein supplying the pace pulse to second lead comprises supplying a pulse having a different waveform than the pace pulse supplied to the unipolar lead.

3. The method of claim 1 wherein supplying the pace pulse to the unipolar lead comprises supplying a pace pulse having a trailing edge comprising at least one of: (a) a gradual decay; (b) a ramp; (c) steps; or (d) a non-linear function.

4. The method of claim 3 wherein supplying the pace pulse to the unipolar lead comprises supplying a pace pulse having a trailing edge comprising an exponential decay.

5. The method of claim 1 wherein supplying the pace pulse to the unipolar lead comprises supplying the pace pulse without a fast recharge period.

6. The method of claim 1 comprising constructing the pace pulse to the unipolar lead to comprise a trailing edge having a duration in a range from about one microsecond to about 3 milliseconds.

7. The method of claim 6 wherein supplying the pace pulse to the unipolar lead comprises supplying a pace pulse having a trailing edge comprising at least one of: (a) a gradual decay; (b) a ramp; (c) steps; or (d) a non-linear function.

8. The method of claim 1 comprising constructing the pace pulse to the unipolar lead to comprise a trailing edge having a duration in a range from about ten microseconds to about one millisecond.

* * * * *